United States Patent
Tarassenko et al.

(10) Patent No.: US 7,647,185 B2
(45) Date of Patent: Jan. 12, 2010

(54) COMBINING MEASUREMENTS FROM DIFFERENT SENSORS

(75) Inventors: Lionel Tarassenko, Oxford (GB); Neil William Townsend, Oxford (GB); James David Price, Oxford (GB)

(73) Assignee: Oxford Biosignals Limited, Oxon (GB)

( * ) Notice: Subject to any disclaimer, the term of this patent is extended or adjusted under 35 U.S.C. 154(b) by 366 days.

(21) Appl. No.: 10/311,250

(22) PCT Filed: Jun. 8, 2001

(86) PCT No.: PCT/GB01/02544

§ 371 (c)(1),
(2), (4) Date: Apr. 10, 2003

(87) PCT Pub. No.: WO01/97059

PCT Pub. Date: Dec. 20, 2001

(65) Prior Publication Data

US 2003/0187337 A1      Oct. 2, 2003

(30) Foreign Application Priority Data

Jun. 16, 2000   (GB) ................................. 0014855.1

(51) Int. Cl.
G01N 33/48 (2006.01)
(52) U.S. Cl. ....................................................... 702/19
(58) Field of Classification Search .................. 702/19; 600/300

See application file for complete search history.

(56) References Cited

U.S. PATENT DOCUMENTS

| 4,791,573 A | 12/1988 | Zemany et al. |
| 4,949,710 A | 8/1990 | Dorsett et al. |
| 5,355,893 A | 10/1994 | Mick et al. |
| 5,396,893 A | 3/1995 | Oberg et al. |
| 5,626,140 A | 5/1997 | Feldman et al. |
| 5,853,364 A | 12/1998 | Baker, Jr. et al. |
| 5,919,141 A | 7/1999 | Money et al. |
| 6,299,582 B1 | 10/2001 | Brockway et al. |
| 6,839,659 B2 | 1/2005 | Tarassenko et al. |
| 6,928,370 B2 | 8/2005 | Anuzis et al. |
| 2004/0148140 A1 | 7/2004 | Tarassenko et al. |
| 2005/0027205 A1 | 2/2005 | Tarassenko et al. |

FOREIGN PATENT DOCUMENTS

| EP | 0 434 856 A1 | 12/1989 |
| EP | 0469794 A2 | 2/1992 |
| WO | WO 94 23495 | 10/1994 |
| WO | WO 00 27281 | 5/2000 |
| WO | 01/30231 A2 | 5/2001 |
| WO | 01/76471 A1 | 10/2001 |
| WO | 03/051198 | 6/2003 |

OTHER PUBLICATIONS

Moody et al; "Clinical Validation of the ECG-Derived Respiration (EDR) Technique"; Computers in Cardiology 1986, vol. 13, pp. 507-510, Washington, DC, IEEE Computer Society Press, http://physionet.incor.usp.br/physiotools/edr/cic86/edr86.html.

Moody et al; Derivation of Respiratory Signals Form Multi-Lead ECGs; Computers in Cardiology 1985, vol. 12, pp. 113-116, Washington, DC, IEEE Computer Society Press, http://physionet.incor.usp.br/physiotools/edr/cic86/edr86.html.

U.S. Appl. No. 10/498,673, allowed claims.

*Primary Examiner*—Jerry Lin
(74) *Attorney, Agent, or Firm*—Nixon & Vanderhye P.C.

(57) ABSTRACT

A method for combining measurements from two or more independent measurement channels, particularly physiological measurements such as heart rate. Independent measurements of heart rate, for instance by ECG and pulse oximetry, can be combined to derive an improved measurement eliminating artefacts on one channel. A model of the process generating the physiological parameter, e.g., the heart rate, is constructed and is run independently for each channel to generate predictions of the parameter. The measured values are compared with the predicted values and the differences are used as an indication of the confidence in the measurement. The measurements from the two channels are ombined using weights calculated from the respective differences.

29 Claims, 4 Drawing Sheets

COMBINING MEASUREMENTS FROM DIFFERENT SENSORS

This application is the U.S. national phase of international application PCT/GB01/02544 filed Jun. 8, 2001, which designated the U.S.

BACKGROUND AND SUMMARY

The present invention relates to a method and apparatus for combining measurements from different sensors in order to provide an improved measurement of a parameter. It is particularly applicable to the measurement of physiological parameters.

Certain parameters can be measured in more than one way. This is useful in giving independent measures of the same quantity. For instance, in the medical field the heart rate can be measured both from an electrocardiogram (ECG) and from a pulse oximetry waveform (used to calculate oxygen saturation). drawings FIG. 4 illustrates schematically these-two-waveforms, FIG. 4a being the electrocardiogram with the heart rate illustrated as $HR_1$, and FIG. 4b the pulse oximetry waveform with the heart rate illustrated as $HR_2$. The heart rate is a parameter which can undergo sudden changes. Some of these changes are valid physiological changes, for example ectopic beats which occur prematurely, and therefore give rise to a temporary increase in the heart rate. FIG. 5 illustrates the occurrence of an ectopic beat 50 found in both the electrocardiogram trace and the pulse oximetry waveform. The shorter interval between the preceeding beat and the ectopic beat 50 manifests itself in a measurement of the heart rate as a sudden increase in the heart rate. FIGS. 1 and 2 of the accompanying drawings show time plots of the heart rate measured by pulse oximetry (FIG. 1) and ECG (FIG. 2). It can be seen that in FIGS. 1 and 2 the heart rate in. the early part of the plot is generally of the order of 80 bpm, but that there are occasional sudden increases in heart rate, such as indicated at 10 and 20 which are caused by ectopic beats and thus appear both in the measurement by pulse oximetry and the measurement by ECG.

However, in addition to changes in the measured heart rate deriving from valid physiological changes, other changes occur which are not physiologically valid, for instance being caused by sudden movement of the sensors on the body surface (e.g. chest movement with ECG electrodes). FIG. 6 illustrates the presence of artefacts 60 on the pulse oximetry waveform which shorten the interval between apparent beats and thus result in apparent increases in the heart rate. These changes are reflected in one measurement, but not the other, as indicated at 12 and 22 in FIGS. 1 and 2 respectively. The fact that the changes appear in one measurement but not the other means that the two measurements could be combined to help decide which heart rate changes are valid physiological ones, and which are artefacts. However, the normal approach of validating one measurement channel against the other involving cross-correlation of the two measurements invariably fails because it is not possible to know in advance (for each recording, for each patient) what value to give to the threshold for accepting, rather than rejecting a change in the heart rate as being valid. Thus although it would appear from FIGS. 1 and 2 that a threshold could be set which would eliminate changes such as indicated as 22, such a threshold is not appropriate for all patients for all recordings, and does not help with the pulse oximetry waveform. The problems are increased in the event of atrial fibrillation when the heart rate changes rapidly as indicated in the region AF in FIGS. 1, 2 and 3.

Similar problems arise in other fields where a parameter is measured via two or more measurement channels.

The present invention provides a method and apparatus for improving measurement of a parameter by combining two measurements of it in a way which allows valid changes to be distinguished from artefacts. Accordingly it provides a method of measuring a parameter comprising the steps of: predicting the value of each of two measurements of the parameter, making two measurements of the parameter to produce two measured values of the parameter, calculating the respective differences between the predicted values and the measured values, and combining the two measured values with weights determined by said differences.

Thus with the present invention a prediction is made for each measurement and the actual measurement is compared with its prediction. The difference is computed, which is termed the "innovation", and this innovation is used to calculate a weight which will be given to that measurement when it is combined with the other measurement, also weighted according to its innovation. The weights are calculated so that if the innovation on one measurement channel is high, whereas the innovation on the other measurement channel is low, the measurement from the low innovation channel is more heavily weighted. This is because a high level of innovation from one channel coinciding with a low innovation on the other channel is regarded as indicative of an artefact on the higher innovation channel. Thus, the weight given to each value when the values are combined is inversely related to the square or modulus of the difference between the measured value and its predicted value.

In one embodiment the measured values can be combined according to the formula:

$$M = M_1 \frac{\sigma_2^2}{\sigma_1^2 + \sigma_2^2} + M_2 \frac{\sigma_1^2}{\sigma_1^2 + \sigma_2^2} \quad (1)$$

where $M_1$ and $M_2$ are the two measured values, and $\sigma_1$ and $\sigma_2$ are the differences between the two measured values and their respective predicted values.

The steps of prediction, measurement, calculation and combination are preferably repeated continuously, with the predicted value for each of the measurements being based on a linear predictive model, e.g the predicted value is based on its preceding predicted value and the preceding innovation (i.e. the difference between the preceding predicted value and the preceding measurement). The predicted value can be obtained by adding to the preceding predicted value a constant times the innovation. The constant is preferably a positive value less than or equal to unity. Alternatively the predicted value for each of the two independent measurements can be calculated by using. a non-linear, predictive model such as a neural network.

In one embodiment the predicted values can be based on a mathematical model of the system, which may include estimates for process noise and sensor (measurement) noise. Two independent models may be used, one for each of the measurement channels, and the models can include estimates for the process noise and sensor noise, which can be the same for the two channels. In one embodiment the models are Kalman filters.

The method is particularly applicable to the measurement of heart rate, in which case the two measurement channels can be from an electrocardiogram and a pulse oximetry waveform, though it is applicable to any other measurement of a parameter which can be derived from two or more sources. Thus the method is applicable for more than two measurement channels, and both where the measurements are independent and where they are not truly independent such as from multiple leads of an ECG.

The invention can also provide for detection of movement artefacts. In this instance high values of innovation are obtained on both channels for the period of movement, and this can be used as a trigger to discard the sections of data which are corrupted by that movement.

It will be appreciated that the invention can be embodied using computer software and thus the invention extends to a computer program for controlling and executing the method or parts of it, and to a computer readable storage medium carrying the program. The invention also extends to corresponding apparatus for carrying out the method.

BRIEF DESCRIPTION OF THE DRAWINGS

The invention will be further described by way of non-limitative example with reference to the accompanying drawings in which.

DETAILED DESCRIPTION OF EXAMPLE EMBODIMENTS

Figure 1:
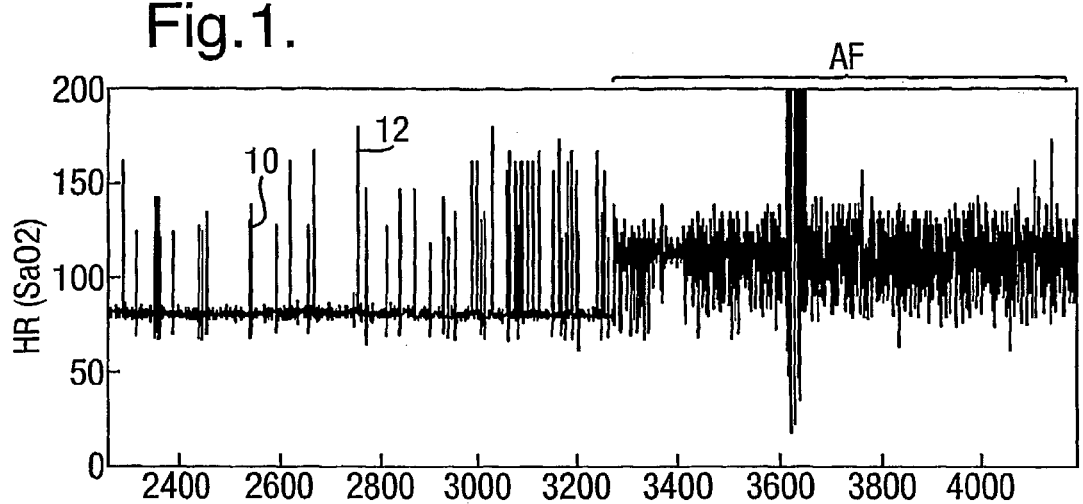
FIG. 1 illustrates a plot of heart rate measured by pulse oximetry.
Figure 2:
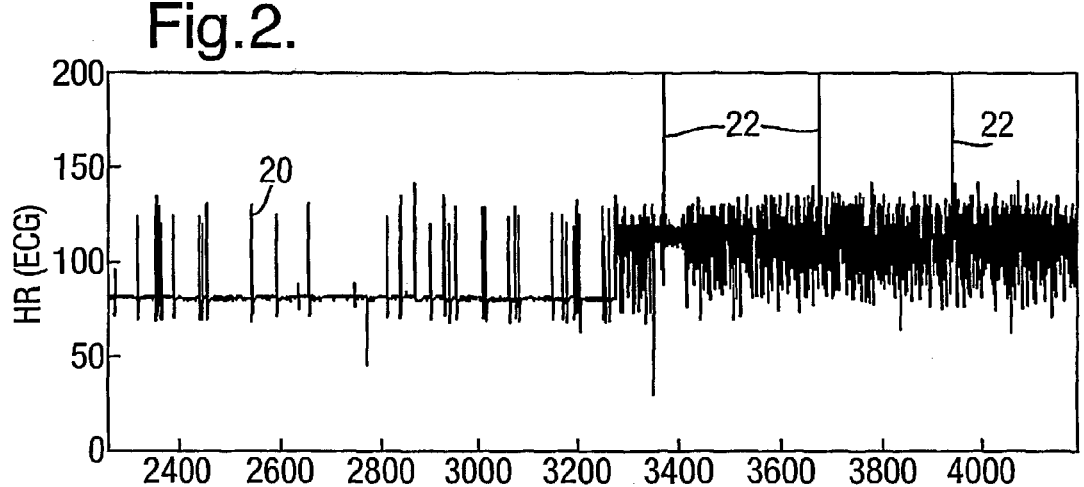
FIG. 2 illustrates a plot of heart rate measured by an ECG.
Figure 4A:
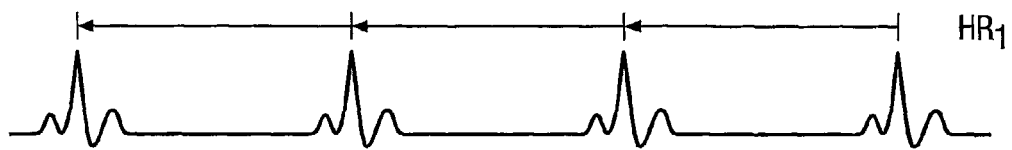
FIG. 4 illustrates schematically heart beats on an ECG and pulse oximetry waveform.
Figure 4B:
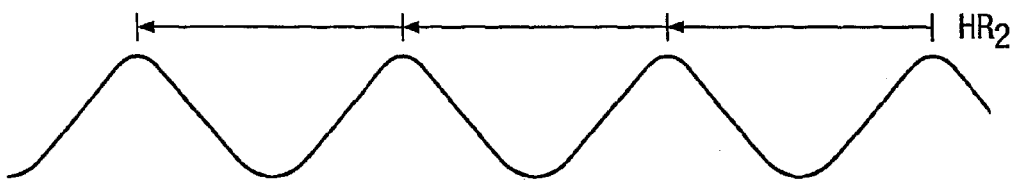
Figure 5A:
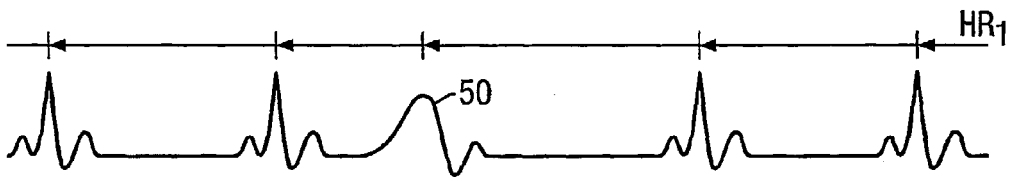
FIG. 5 illustrates schematically ectopic beats appearing on an ECG and pulse oximetry waveform.
Figure 5B:
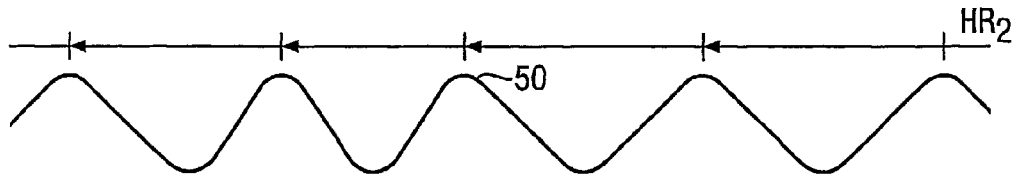
Figure 6:
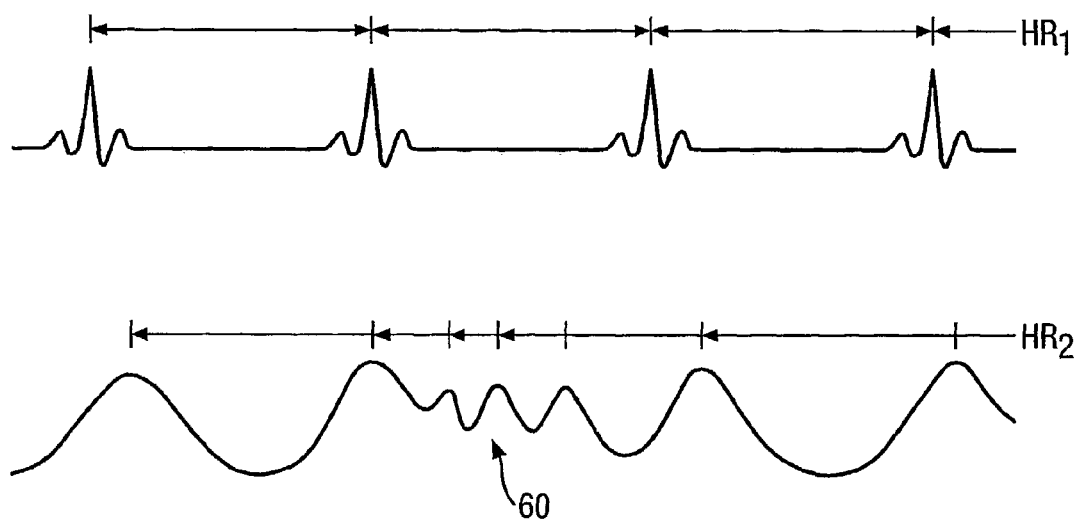
FIG. 6 illustrates an ECG trace and pulse oximetry waveform with artefacts on the pulse oximetry waveform.

An embodiment of the invention will now be described in which the invention is applied in the medical field to the measurement of heart rate using ECG and pulse oximetry. As illustrated in FIG. 4a the heart rate measured by ECG is derived from the interval between two successive R-wave peaks. The heart rate measurement derived from the pulse oximetry waveform is obtained from the interval between two successive peaks (or troughs) as illustrated in FIG. 4b. FIGS. 1 and 2 illustrate heart rate plots derived from these two measurements.

With this embodiment of the present invention a model of the process generating the heart rate is constructed. The same model is run independently for each measurement source (i.e. one for the ECG measurement channel and one for the pulse oximetry measurement channel). In this embodiment the model is a Kalman filter. In general a Kalman filter uses a process model and an observation model. The process model models the state of the system at time t+1 in terms of its state at time t. The measurement or observation model indicates how the measurement at time t is related to the state of the system at time t. Thus in general terms:

$X_{t+1} = Ax_1 + w$ (Process model)
$Y_t = Cx_t + v$ (Observation model)

where:
$w \sim N(O, Q)$ — Gaussian process noise with zero mean and variance Q
$v \sim N(O, R)$ — Gaussian measurement noise with zero mean and variance R and:
k—vector of state variables x
n—vector of observable or measurements y
State x evolves according to simple first-order Markov dynamics;
A is the k×k state transition matrix
Each measurement vector y is related to the current state by a linear observation process; C is the n×k observation or measurement matrix In this embodiment the general Kalman filter is simplified to use scalar quantities and the same process and measurement noise models (w, v) are used on both measurement channels. Thus the simplified Kalman filter is as follows:

$x_{t+1} = Ax_t + w$ (Process model)
$y_t = Cx_t + v$ (Observation model)

The model is further simplified by setting C=1, implying that the heart rate is both the state describing the process and the measurement. Further, it is assumed that A=1, implying that the next heart rate is the same as the previous one with the variability allowed for by the process noise model.

Using this model, on each channel, the process of combining the two measurements then involves the following steps:

1. From knowledge of previous history up to time t (a) predict the next state xpred; (b) from xpred predict the next measurement ypred
2. Make the measurement $y_{t+1}$
3. Compute the innovation:

$y_{t+1} = ypred + \epsilon_{t+1}$ where $\epsilon_{t+1}$ is the difference between the actual value and the predicted value: the innovation.
4. Compute the variance $\sigma_{t+1}^2$:

$\sigma_{t+1}^2 = \epsilon_{t+1}^2$ $\sigma^2$ the variance, is the inverse of the "confidence" which is associated with the prediction
5. Mix the heart rate measurements in inverse proportion to the variance associated with each one:

$$HR = HR_1 \frac{\sigma_2^2}{\sigma_1^2 + \sigma_2^2} + HR_2 \frac{\sigma_1^2}{\sigma_1^2 + \sigma_2^2}$$

An example of an implementation of this model in MATLAB is given in Appendix 1. That example is general, and will work for vector quantities, though in this embodiment the quantities are scalar. It can be seen from appendix 1 that the predicted heart rate for each new measurement cycle (xnew) is equal to the previously predicted value (xpred) plus the Kalman gain K times the innovation e. The Kalman gain K is derived from the predicted variance Vpred and the measurement variance R. The predicted variance is derived from the previous predicted variance and the process noise Q. To start the process off it is initialized using an initial value of the heart rate as 80 and an initial value of the state variance of 100. The process noise in the Q in this embodiment is set to 5 and the measurement noise variance R is set to 10.

It will be clear from the implementation that, as normal with a Kalman filter, the variance and Kalman gain are not dependent on the measurement values. The measurement values are only used in the new prediction of heart rate via the innovation e. Thus it will be noted that for the constant values of Q and R used in this example the Kalman gain K tends to 0.5 and the state co-variance V tends to 5. However, K can be made adaptive by modifying the values for the variance constants Q and R, preferably the process variance Q, according to the type of process being encountered, for example atrial fibrillation (where there is a high level of process noise) as opposed to a healthy heart rate (during which there is a low level of process noise).

Figure 7:
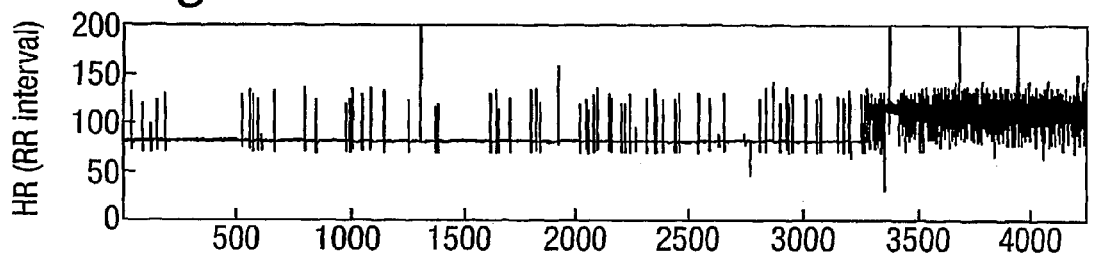
FIG. 7 illustrates a plot of heart rate measured by an ECG.
Figure 8:
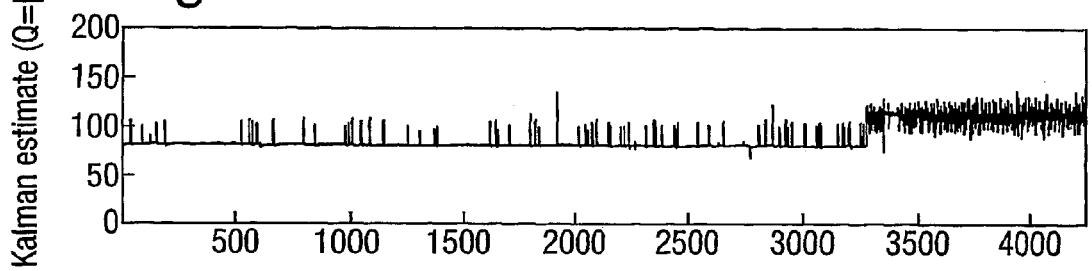
FIG. 8 illustrates predicted values for the heart rate according to one embodiment of the invention.
Figure 9:
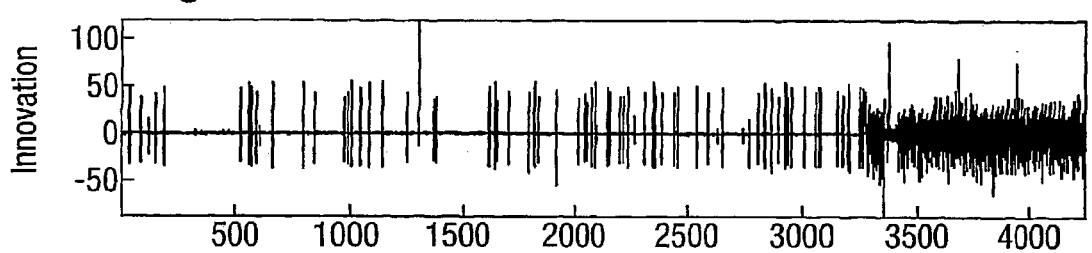
FIG. 9 illustrates the innovation obtained from FIGS. 7 and 8.
Figure 10:
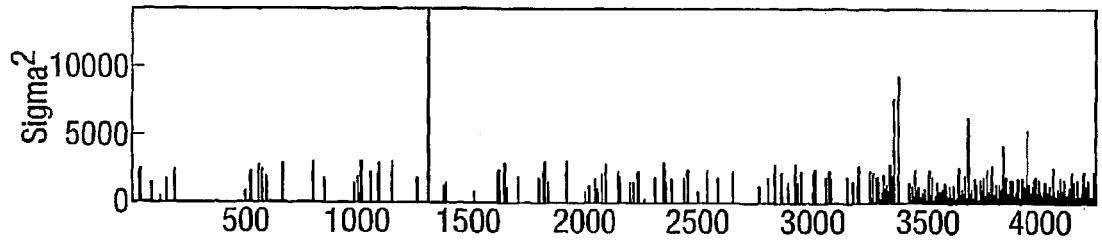
FIG. 10 illustrates the variance obtained from FIGS. 7 and 8.

FIGS. 8, 9 and 10 illustrate values for the estimated heart rate xpred, the innovation e and the variance $\sigma^2$ for the heart rate plot shown in FIG. 7 (in this case the ECG measurement channel).

Figure 3:
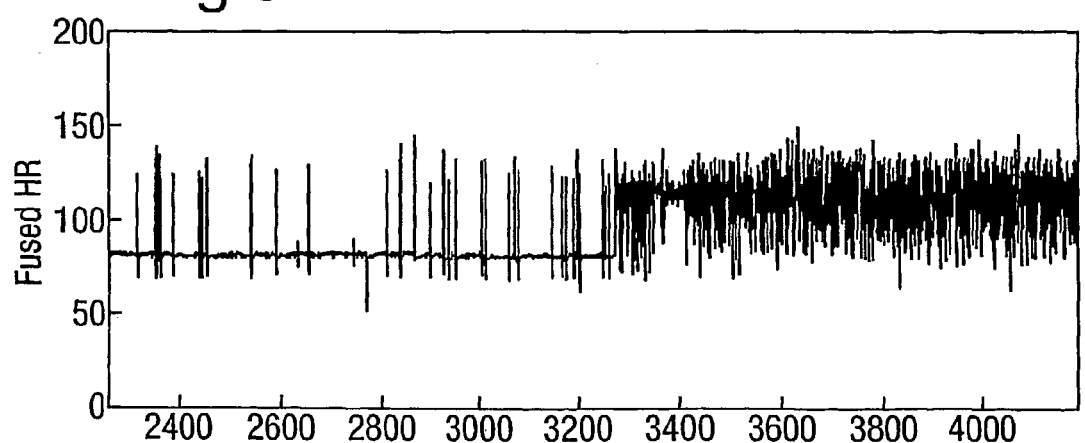
FIG. 3 illustrates the result of combining the two plots of FIGS. 1 and 2 according to an embodiment of the invention.

FIG. 3 illustrates the result of combining the two measurement plots from FIGS. 1 and 2 using this embodiment. It can be seen that the movement artefacts 22 on the ECG channel in FIG. 2 have been removed from the combined measurement, even though they occur during a period of atrial fibrillation.

Thus with this embodiment the difference between the measurement and its predicted value is used to indicated the degree of confidence in that measurement. The higher the difference the lower the confidence. Formula (1) above-is used to combine the two measurements. This can be summarised as follows:

1) Valid heart rates on both channels: low innovation on both channels; weight both measurements equally
2) Valid sudden change (e.g. ectopic beat) seen on both channels: high innovation but on both channels; therefore, measurements are again weighted equally
3) Artefact on one channel: high innovation on one channel only; therefore the information from that channel is ignored by being given a very low weighting (low confidence).

The method can also be used to provide a movement artefact detector, i.e. to detect when movement artefact is present on both channels and therefore no useful information is available. This is characterised by high values of innovation on both channels for a sustained period of time. This can be used to discard the sections of raw data which are corrupted by this movement and to indicate that no valid heart rate estimate can be derived during those periods.

Appendix 1

```
load -ascii ecghr_13
data_file = ecghr_13;
time = data_file(:,1);
hr = data_file(:,2);
start = 1
stop = size(data_file),1);
fprintf('number of R—R intervals detected = %d \n', stop);
hr_limit = 200;
                % X(t + 1) = A X(t) + noise(Q) - process model with
                  Q as variance of noise w
                % Y(t) = C X(t) + noise(R) - measurement model with
                  R as variance of noise v
ss = 1;         % state size - sets to one dimensional, ie scalar though
                  routine works for vectors
os = 1;         % observation size - sets to one dimensional, ie scalar
A = [1];        % assume x(t + 1) = x(t)
C = [1];        % assume y = x
Q = 5.0*eye(ss); % process noise - eye is the identity matrix in
                  MATLAB-here just unity
R = 10.0*eye(os); % measurement noise variance
initx = [80];   % initial state value (HR of 80 bpm)
initV = 100*eye(ss); % initial state variance
xnew = initx;   % - initialisation
Vnew = initV;
for i = start:stop %-start of cycle
    x = xnew;           % update from previous cycle
    V = Vnew;           % update from previous cycle
```

Appendix 1-continued

```
    xpred = A*x;         % prediction of state
    Vpred = A*V*A' + Q;  % prediction of state covariance, A' is
                           transpose of A
    ypred(i) = C*xpred;  % prediction of measurement
    y(i) = hr(i);        % "make measurement"
    e = y(i) − ypred(i); % calculate innovation
    innov(i) = e;        % for plotting
    sigma2(i) = e*e;     % variance for saving
    S = C*Vpred*C' + R;  % innovation covariance
    Sinv = inv(S);       % invert S
    K = Vpred*C' *Sinv;  % compute Kalman gain
    xnew = xpred + K*e;  % update state by the innovation controlled
                           by the Kalman gain
    Vnew = (eye (ss) − K*C) *Vpred;  % update state covariance
    end
end
```

We claim:

1. A method of measuring a parameter comprising using a suitably programmed computer to perform steps including: predicting a value of each of two independent measurements of the parameter for two independent measurement channels, making two independent measurements of the parameter via said two independent measurement channels to produce two measured values of the parameter, calculating respective differences between the predicted values and the measured values for each of said two independent measurement channels, combining the two measured values with weights which vary inversely with said respective differences to produce a combined value, and outputting the combined value to a user.

2. A method according to claim 1 in which the predicting, the making of two independent measurements, the calculating and the combining are repeated, the predicted value for each of the two independent measurements being based on a preceding predicted value and a difference between the preceding predicted value and a preceding measured value.

3. A method according to claim 2 in which the predicted value for each of the two independent measurements is calculated by using a linear predictive model for each of said two independent measurement channels.

4. A method according to claim 2 in which the predicted value for each of the two independent measurements is calculated by using a non-linear predictive model for each of said two independent measurement channels.

5. A method according to claim 3 in which each model is adaptive, and it adapts in dependence upon the amount of process noise in the respective measurement channels.

6. A method according to claim 1 in which in the step of combining the two measured values the weights are inversely proportional to the squares of said respective differences.

7. A method of measuring a parameter comprising using a suitably programmed computer to perform steps including: predicting a value of each of two independent measurements of the parameter for two independent measurement channels, making two independent measurements of the parameter via said two independent measurement channels to produce two measured values of the parameter, calculating respective differences between the predicted values and the measured values for each of said two independent measurement channels, combining the two measured values with weights determined by said respective differences to produce a combined value M, and outputting the combined value to a user, wherein the two measured values are combined according to the formula:—

$$M = M_1 \frac{\sigma_2^2}{\sigma_1^2 + \sigma_2^2} + M_2 \frac{\sigma_1^2}{\sigma_1^2 + \sigma_2^2}$$

where M1 and M2 are the two measured values, and $\sigma_1$ and $\sigma_2$ are differences between the two measured values and their respective predicted values.

8. A method according to claim 1 in which the predicted values for the respective measurements are based on respective models for measurement of said parameter via said two independent measurement channels.

9. A method according to claim 8 in which the models include estimates for process noise and sensor noise for said two independent measurement channels.

10. A method according to claim 8 in which the respective models are mutually independent.

11. A method according to claim 10 in which the respective models include the same estimates for process noise and sensor noise.

12. A method of measuring a parameter comprising using a suitably programmed computer to perform steps including: predicting a value of each of two independent measurements of the parameter for two independent measurement channels using respective models for measurement of the parameter, making two independent measurements of the parameter via said two independent measurement channels to produce two measured values of the parameter, calculating respective differences between the predicted values and the measured values for each of said two independent measurement channels, combining the two measured values with weights which vary inversely with said respective differences to produce a combined value, and outputting the combined value to a user, wherein the respective models comprise Kalman filters.

13. A method according to claim 1 further comprising discarding series of measurements for which the differences between both measured values and their predicted values exceed a predetermined threshold for a predetermined period of time.

14. A method according to claim 1 in which the parameter is heart rate.

15. A method according to claim 14 in which the two independent measurements are made from an electrocardiograph and a pulse oximetry waveform respectively constituting said two independent measurement channels.

16. A method according to claim 14 in which the two measurements are made from a multiple lead ECG recording.

17. A method according to claim 1 in which there are more than two measurements.

18. A method according to claim 1 further comprising identifying movement artifacts based on the values of the differences between both measured values and their predicted values.

19. A computer program encoded on a computer-readable storage medium and comprising program code which, when executed, performs the method of claim 1.

20. Apparatus configured to perform the method of claim 1.

21. A method according to claim 4 in which each model is adaptive, and it adapts in dependence upon the amount of process noise in the respective measurement channels.

22. A method of measuring a physiological parameter comprising using a suitably programmed computer to perform steps including: predicting by use of respective Kalman filters a value of each of two independent measurements of the physiological parameter for two independent measurement channels, making two independent measurements of the physiological parameter via the two independent measurement channels to produce two measured values of the physiological parameter, calculating respective differences between the predicted values and the measured values for each of the two independent measurement channels, combining the two measured values with weights which vary inversely with which vary inversely with the respective differences to produce a physiological parameter measurement, and outputting the physiological parameter measurement to a user.

23. The method according to claim 22, in which the physiological parameter is heart rate.

24. The method according to claim 22, in which a first of the two measurement channels corresponds to an electrocardiograph and a second of the two measurement channels corresponds to pulse oximetry.

25. A computer-readable storage medium on which computer-executable instructions for performing the method according to claim 22 are encoded.

26. A method of measuring a parameter comprising using a suitably programmed computer to perform steps including:
  predicting a value of each of two independent measurements of the parameter for two independent measurement channels;
  making two independent measurements of the parameter via said two independent measurement channels to produce two measured current values of the parameter;
  calculating respective differences between the predicted values and the measured current values for each of said two independent measurement channels; and
  combining the two measured current values with weights which vary inversely with said respective differences to produce and output to a user a measurement of the parameter which is based on the two measured current values.

27. A method of measuring a parameter comprising using a suitably programmed computer to perform steps including:
  predicting a value of each of two independent measurements of the parameter for two independent measurement channels;
  making two independent measurements of the parameter via said two independent measurement channels to produce two measured current values of the parameter;
  calculating respective differences between the predicted values and the measured current values for each of said two independent measurement channels;
  combining the two measured current values with weights which vary inversely with said respective differences to produce a measurement of the parameter which is based on the two measured current values; and
  displaying the measurement of the parameter.

28. A method according to claim 27 wherein the measurement of the parameter is displayed as part of a plot.

29. A computer-readable storage medium on which computer-executable instructions for performing the method according to claim 27 are encoded.

* * * * *